US009321714B1

(12) United States Patent
Brandvold et al.

(10) Patent No.: US 9,321,714 B1
(45) Date of Patent: Apr. 26, 2016

(54) PROCESSES AND CATALYSTS FOR CONVERSION OF 2,5-DIMETHYLFURAN DERIVATIVES TO TEREPHTHALATE

(71) Applicant: UOP LLC, Des Plaines, IL (US)

(72) Inventors: Timothy A. Brandvold, Arlington Heights, IL (US); Avram M. Buchbinder, Chicago, IL (US); Nancy Iwamoto, Ramona, CA (US); Hayim Abrevaya, Kenilworth, IL (US); Phuong T. M. Do, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/562,358

(22) Filed: Dec. 5, 2014

(51) Int. Cl.
*C07C 51/09* (2006.01)
*C07C 67/04* (2006.01)
*C07D 307/68* (2006.01)

(52) U.S. Cl.
CPC .................. *C07C 51/09* (2013.01); *C07C 67/04* (2013.01); *C07D 307/68* (2013.01)

(58) Field of Classification Search
CPC ....... C07C 51/09; C07C 67/04; C07D 307/68
See application file for complete search history.

(56) References Cited

U.S. PATENT DOCUMENTS

| | | | |
|---|---|---|---|
| 7,385,081 | B1 | 6/2008 | Gong |
| 8,314,267 | B2 | 11/2012 | Brandvold |
| 2010/0331568 | A1 | 12/2010 | Brandvold |
| 2013/0171397 | A1 | 7/2013 | Ghosh et al. |
| 2013/0245316 | A1 | 9/2013 | Masuno et al. |
| 2013/0345447 | A1 | 12/2013 | Shaikh et al. |
| 2013/0345448 | A1 | 12/2013 | Shaikh et al. |
| 2013/0345449 | A1 | 12/2013 | Partin et al. |
| 2014/0296600 | A1 | 10/2014 | Dauenhauer et al. |
| 2015/0141670 | A1* | 5/2015 | Davis et al. |

FOREIGN PATENT DOCUMENTS

| | | |
|---|---|---|
| CN | 102977244 A | 3/2013 |
| EP | 2370496 A1 | 10/2011 |
| EP | 2481733 A1 | 8/2012 |
| KR | 2012107573 A | 10/2012 |
| WO | WO 2007/104514 A2 | 9/2007 |
| WO | WO 2009/110402 A1 | 9/2009 |
| WO | WO 2013/040514 A1 | 3/2013 |
| WO | WO 2013/097013 A1 | 7/2013 |
| WO | WO 2013/159081 A2 | 10/2013 |

OTHER PUBLICATIONS

Eerhart et al., "Replacing fossil based PET with biobased PEF; process analysis, energy and GHG balance", Energy & Environmental Science (2012), vol. 5, 6407-6422.
Li et al., "Synthesis of poly(octylene 2, 5-furandicarboxylate)", Chinese Journal of Applied Chemistry (2013), 30(6), 661-666.
Li, Wei-jie, "Synthesis of furan-2, 5-dicarboxylic acid and its dimethyl ester catalyzed by ferrous chloride," Huaxue Shiji Journal (2013), 35(8), 767-768.
De Jong et al., "Chapter 1: Furandicarboxylic Acid (FDCA), A Versatile Building Block . . . ," Biobased Monomers, Polymers, and Materials (2012), ACS Symposium Series, 13 pages.
Do et al., "Elucidation of Diels-Alder Reaction Network of 2,5-Dimethylfuran and Ethylene on HY Zeolite Catalyst," ACS Catalysis (2013), vol. 3, 41-46.
Mushrif et al., "Understanding solvent effects in the selective conversion of fructose . . . ," Physical Chemistry Chemical Physics (2012), vol. 14, 2637-2644.
Besson et al., "Conversion of Biomass into Chemicals over Metal Catalysts," Chemical Reviews (2014), 114(3), 1827-1870.
Chang et al., "Ultra-Selective Cycloaddition of Dimethylfuran for Renewable p-Xylene with H-BEA," Green Chemistry (2013), 16(2), 585-588.
Liu et al., "Catalytic conversion of sugar into hydromethylfurfural in ionic liquids," Catalysis Today (2012), vol. 200, 106-116.
Khan et al., "Liquid-phase dehydration of sorbitol to isosorbide using sulfated zirconia as a solid acid catalyst," Applied Catalyst A: General (2013), 452, 34-38.
Kumari et al., "Vapor Phase Synthesis of Phthalate Esters from Benzene and Maleic Anhydride . . . ," Reaction Kinetics and Catalysis Letters (2002), 76(2), 221-225.
Bini et al., "A rationalization of the solvent effect on the Diels-Alder reaction in ionic liquids . . . ," Organic & Biomolecular Chemistry (2008), 6, 2522-2529.
Lin et al., "Aromatics from Lignocellulosic Biomass . . . " American Institute of Chemical Engineers Journal (2013), 59(6), 2079-2087.
Nikbin et al., "A DFT study of the acid-catalyzed conversion of 2,5-dimethylfuran and ethylene . . . " Journal of Catalysis (2013), 297, 35-43.
Mahmoud et al., "Renewable production of phthalic anhydride from biomass-derived furan and maleic anhydride," Green Chemistry (2014), 16, 167-175.
Roman-Leshkov et al., "Production of dimethylfuran for liquid fuels from biomass-derived carbohydrates," Nature (2007), 447, 982-985.
Vidis et al., "Effect of Lewis acids on the Diels-Alder reaction in ionic liquids with different activation modes," Journal of Physical Organic Chemistry (2008), 21, 264-270.
Harifi-Mood et al., "Kinetics study of a Diels-Alder reaction in mixtures of an ionic liquid . . . ," Journal of Physical Organic Chemistry (2008), 21, 783-788.
Acevedo et al., "Elucidation of Rate Variations for a Diels-Alder Reaction in Ionic Liquids . . . ," Journal of Chemical Theory and Computation (2007), 3, 132-138.
Williams et al., "Cycloaddition of Biomass-Derived Furans for Catalytic Production of Renewable p-Xylene," ACS Catalysis (2012), 2, 935-939.

(Continued)

*Primary Examiner* — Shailendra Kumar

(57) ABSTRACT

A process of making terephthalic acid or a derivative of terephthalic acid is described. The process includes reacting a derivative of 2,5-dimethylfuran, with a dienophile containing an unsaturated 2-carbon unit, in the presence of a catalyst having Brönsted acidity to form a para-xylene derivative; and optionally reacting the para-xylene derivative to terephthalic acid.

19 Claims, 1 Drawing Sheet

(56) References Cited

OTHER PUBLICATIONS

Roman-Leshkov et al., "Phase Modifiers Promote Efficient Production of Hydroxymethylfufural from Fructose," Science (2006), 312, 1933-1937.

Wang et al., "Selective Production of Aromatics from Alkylfurans over Solid Acid Catalysts," ChemCatChem (2013), 5, 2044-2050.

Pacheco et al., "Synthesis of terephthalic acid via Diels-Alder reactions with ethylene and oxidized variants . . . ," PNAS (2014), 111(23), 8363-8367.

* cited by examiner

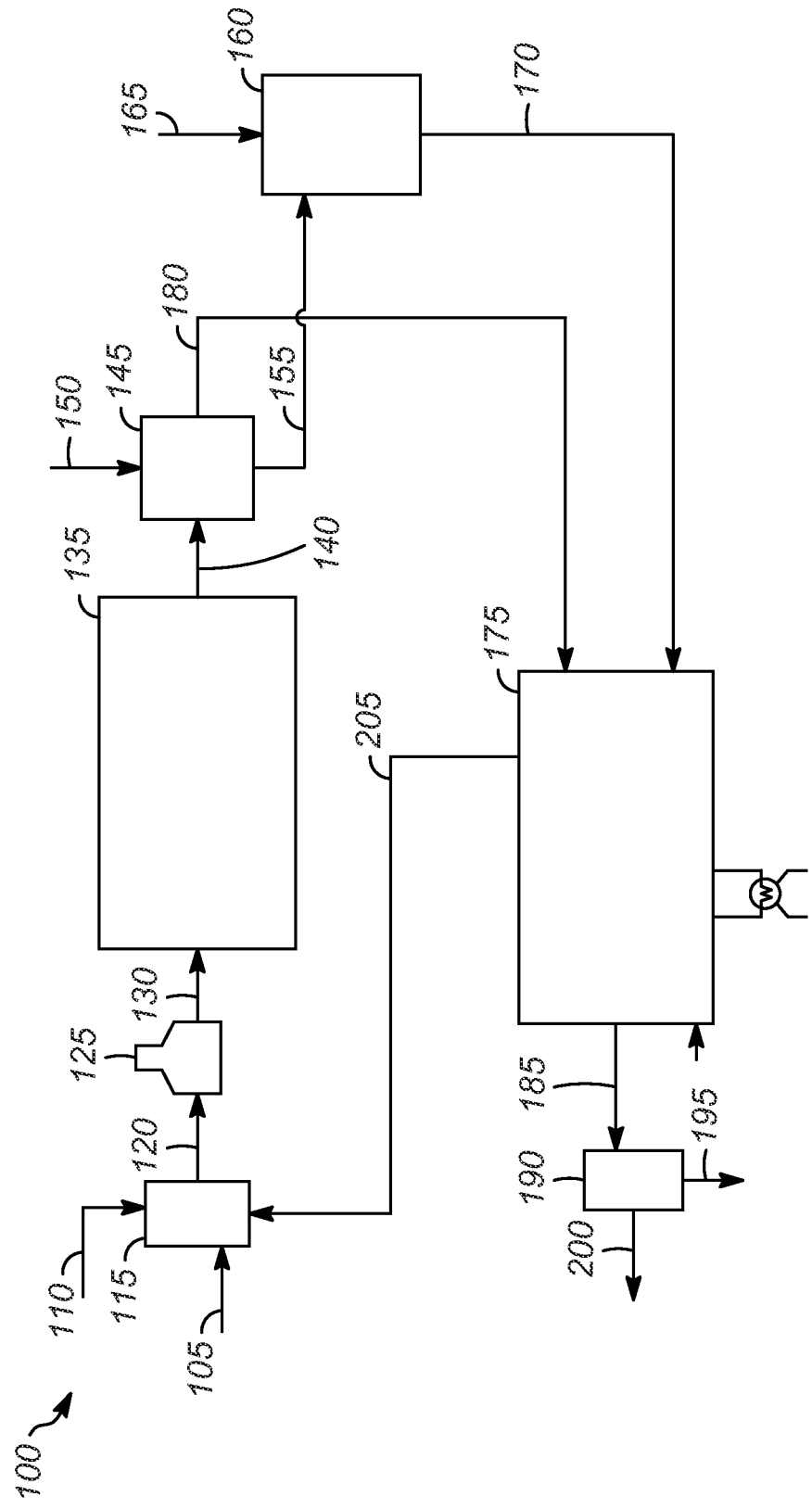

PROCESSES AND CATALYSTS FOR CONVERSION OF 2,5-DIMETHYLFURAN DERIVATIVES TO TEREPHTHALATE

BACKGROUND OF THE INVENTION

Terephthalic acid (PTA), one of the raw materials for polyethylene terephthalate (PET) polymers, is currently produced by the oxidation of petroleum-derived para-xylene. Obtaining isomerically pure para-xylene (pX) from benzene-toluene-xylene (BTX) feeds requires several integrated processes such as disproportionation of toluene, isomerization of xylenes, and separation of para-xylene from an equilibrium mixture of xylenes. Oxidation of para-xylene to PTA is capital intensive, requiring both liquid phase oxidation in acetic acid and purification of crude terephthalic acid by selective hydrogenation. Furthermore, this process is petroleum based. There is a demand for PET from renewable sources, which may also have a cost advantage for the feedstock.

U.S. Pat. No. 7,385,081 (the '081 patent) describes the reaction of oxygenated derivatives of 2,5-dimethylfuran (DMF) to form terephthalic acid. However, that process did not utilize a catalyst, and, as a result, the yield obtained was extremely small. The '081 patent stated that the yield of terephthalic acid (and no other terephthalates) was 0.14 mol % using 2,5-furandicarboxylic acid (FDCA—CAS 3238-40-2) as the feed. Although the patent did not provide it, the yield of terephthalic acid using furan-2,5-dicarboxylate dimethyl ester (DM-FDCA—CAS 526-99-8) as the feed was calculated to be at most 0.023 mol % yield of terephthalic acid (and no other terephthalates) based on the data included in the patent. There are also several demonstrations in the prior art for conversion of DMF to para-xylene. Like U.S. Pat. No. 7,385,081, these processes utilize a cycloaddition pathway with ethylene acting as a dienophile adding to a furan as a diene, but in these cases the diene is DMF rather than an oxygenated derivative. These processes involve the activation of the diene (DMF) by electron-donating alkyl groups which leads the diene to become more reactive toward the dienophile compared to FDCA or DM-FDCA. However, the product is para-xylene rather than a terephthalate, and it must be further oxidized and purified in subsequent steps to obtain terephthalic acid. Furthermore, approaches that generate pX from biomass as a feedstock for PTA are not atom-efficient. Biomass (sugar) has a high oxygen content. Any route to PTA via pX must involve removing all of the oxygen from sugar, which generally requires hydrogen and yield losses. The oxygen is then added back in at considerable expense during pX oxidation. One example is the process described in US 2010/0331568 and U.S. Pat. No. 8,314,267 in which activated carbon, $ZnCl_2$, rare-earth exchanged Y zeolite, silica gel, and gamma-alumina were used to catalyze the reaction of DMF and ethylene to form para-xylene. In WO 2009/110402, titanocene dichloride is used to catalyze the same reaction. In Do et al., "Elucidation of Diels-Alder Reaction Network of 2,5-Dimethyfuran and Ethylene on HY Zeolite Catalyst," ACS Catal. 2013, 3, 41-46, HY zeolite is utilized, and the authors suggest a confinement effect of the faujusite cages as enhancing the Diels-Alder reaction (also using DMF as feed). In WO 2013/040514, Lewis acid catalysts such as copper triflate were utilized to obtain high conversion and selectivity for conversion of DMF to para-xylene. In Nikbin et al., A DFT study of the acid-catalyzed conversion of 2,5-dimethylfuran and ethylene to p-xylene," J. Catal, 2013, 297, 35-43, using computational methods, the authors teach that for the reaction of DMF and ethylene to form para-xylene, the dehydration step is catalyzed by Brönsted acids but the cycloaddition step is catalyzed by Lewis acids. Supporting this, in Wang et al., "Selective Production of Aromatics from Alkylfurans over Solid Acid Catalysts," Chem. Cat. Chem. 2013, 5, 2044-2050 the authors show that non-porous materials with both Lewis and Brönsted acidity such as $WOx-ZrO_2$ and niobic acid have high activity and selectivity compared to materials that have only Lewis acidity. At 60% conversion of DMF, their work shows that $WOx-ZrO_2$ is more than 3 times as active as H—Y zeolite, suggesting that Lewis acidity provides additional rate acceleration.

US 2014/0296600 describes a process for making paraxylene via cycloaddition of ethylene and DMF and subsequent dehydration using acidic heterogeneous catalysts and a solvent for DMF. The process is said to have high selectivity and high yields. The use of a solvent shows significant effects in the reduction of competing side reactions including hydrolysis of DMF to 2,5-hexanedione, alkylation of p-xylene, and polymerization of 2,5-hexanedione.

Pacheco and Davis, "Synthesis of terephthalic acid via Diels Alder reactions with ethylene and oxidized variants of 5-hydroxymethyfurfural," PNAS, 111(23), p. 8363-8367 (2014), describe a process in which 5-hydroxymethylfurfural (HMF) is partially oxidized to 5-(hydroxymethyl) furoic acid (HMFA). The HMFA and the ether and ester derivatives of HMFA are reacted with ethylene in a Diels-Alder reaction to produce the desired aromatic product, which is then oxidized to PTA or dimethyl terephthalate. Dioxane is the preferred solvent. The process requires the oxidation of the reaction product of the Diels-Alder reaction. In addition, FDCA did not react.

Therefore, there is a need for processes for making terephthalic acid from non-petroleum feedstocks.

SUMMARY OF THE INVENTION

One aspect of the invention is a process of making terephthalic acid or a derivative of terephthalic acid. In one embodiment, the process includes reacting a derivative of 2,5-dimethylfuran, with a dienophile containing an unsaturated 2-carbon unit, in the presence of a catalyst having Brönsted acidity to form a para-xylene derivative; and optionally reacting the para-xylene derivative to terephthalic acid.

BRIEF DESCRIPTION OF THE DRAWING

The FIGURE is a schematic of one embodiment of the process of present invention.

DETAILED DESCRIPTION OF THE INVENTION

Rather than using para-xylene generated from xylene isomerization and toluene disproportionation reactions in a petroleum-derived aromatics complex, this invention involves a process in which oxygenated derivatives of 2,5-dimethylfuran (DMF), known as the diene, are converted to terephthalic acid (PTA) or other para-xylene derivatives by contacting with a dienophile containing an unsaturated 2-carbon unit in the presence of a catalyst and optionally a solvent, as well as catalysts for this conversion. The feed is typically obtained from saccharide-containing biomass, such as cellulose, through known chemistry. The process provides an increased para-xylene derivative yield, greater than 7 mol %, as a result of utilizing a catalyst.

The process has a number of advantages. It allows for the production of terephthalic acid and para-xylene derivatives without the need for para-xylene oxidation. By utilizing an oxygenated derivative of DMF, such as 2,5-furandicarboxylic acid (FDCA), in some embodiments, no oxidation step is required to obtain terephthalic acid, as would be the case if the reaction product were para-xylene. In those embodiments where oxidation is needed, the oxidation reaction is not as difficult such that less oxygen is required and/or the reaction conditions are less severe. Utilizing an oxygenated derivative of DMF as the feed is also advantageous, as hydrodeoxygenation of a sugar derived furan such as 5-hydroxymethylfurual is not required. Further, esters of FDCA provide faster cycloaddition reactions than FDCA itself. Using a regioselective chemistry and utilizing a feed that is naturally isomerically pure leads to the production of terephthalates with isomer selectivity to the para form. In some embodiments, a bio-renewable feedstock can be used, which may have a feedstock cost advantage or a product price advantage due to demand for renewable materials.

The diene is a derivative of DMF which contains at least one atom that is not hydrogen or carbon bonded to at least one of the methyl carbons. Suitable derivatives of DMF include, but are not limited to, ester derivatives, aldehyde derivatives, carboxylic acid derivatives, ether derivatives, halide derivatives, acid halide derivatives, amide derivatives, alcohol derivatives, anhydride derivatives, aldehyde derivatives, and ether derivatives wherein one or both of the methyl carbons are derivatized, or combinations thereof. As used herein, the term "derivative of DMF" does not necessarily imply that DMF was a starting material to obtain the "derivative of DMF", merely that the derivative of DMF contains a DMF unit with substitution or derivatization at the methyl carbons. In most cases the derivative of DMF is in fact derived from a reactant other than DMF.

In some embodiments, the derivative of DMF is obtained from biomass. For example, FDCA can be obtained from biomass through known methods. Two main known pathways from biomass to FDCA exist: 1) acid hydrolysis of saccharides to obtain 5-hydroxymethyl-2-furfural (HMF) followed by oxidation to FDCA and 2) oxidation of saccharides to mucic acid, followed by acid hydrolysis to FDCA.

In some embodiments, the product of the reaction is a para-xylene derivative. As used herein the term "para-xylene derivative" does not imply that the product was made using para-xylene as a starting material. In some embodiments, the para-xylene derivative is further reacted to obtain terephthalic acid. Some non-limiting embodiments for converting the para-xylene derivative to terephthalic acid are described below; other methods are possible as well.

One derivative of DMF which can be used is FDCA. The FDCA is reacted with ethylene in a Diels-Alder reaction (4+2 cycloaddition) in the presence of a catalyst to form a bicyclic adduct (CAS 1030358-18-9). The adduct then dehydrates to form terephthalic acid or its derivatives and water. In most cases, the dehydration of the adduct occurs in-situ without isolation of the adduct. Alternatively and preferably, FDCA is first converted to its di-ester derivative, such as furan-2,5-dicarboxylate dimethyl ester (DM-FDCA CAS 4282-32-0), prior to reaction.

The reaction scheme below illustrates the FDCA reaction with ethylene to form terephthalic acid with loss of water.

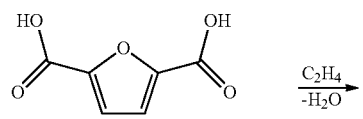

-continued

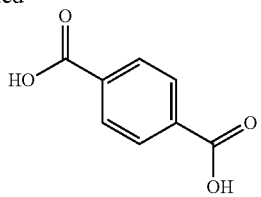

Conversion of FDCA to its ester form prior to reaction results in faster reaction. Although not wishing to be bound by theory, this is likely due to a more favorable orbital overlap between the diene and dienophile which has been shown by computational methods. The ester can be pre-synthesized and isolated or synthesized in situ (for instance by reaction of FDCA in the presence of an alcohol such as methanol or butanol). If the ester is pre-synthesized, rather than formed in situ, additional water is not generated from the reaction to form the ester. Water may decrease the reaction yield of the diene reaction with ethylene due both to poisoning of Brönsted sites on the catalyst and because the equilibrium for the dehydration of the cycloadduct is less favorable in the presence of water. Methods for conversion of FDCA to DM-FDCA are known and can be achieved with renewable reagents (for instance the acid-catalyzed condensation with methanol shown in example 2 of U.S. Pat. No. 7,385,081).

If DM-FDCA is used as the feed, dimethyl terephthalate (DM-TA) is obtained by reaction with ethylene, as well as diethyl-terephthalate (DE-TA) and ethyl-methyl terephthalate (EM-TA). Formation of ethyl esters is likely a result of activation of ethylene to an alcohol or surface bound ethoxide followed by trans-esterification. The ester derivatives of terephthalic acid can be subsequently hydrolyzed by contacting with an aqueous acid or base to obtain terephthalic acid. If a different ester derivative of FDCA is used, a corresponding dialkyl terephthalate ester is obtained by reaction with ethylene and can be similarly hydrolyzed by contacting with an aqueous acid or base to obtain terephthalic acid.

The reaction scheme below illustrates one example of a reaction of an ester derivative of DMF to form terephthalic acid in two steps. R is any substituent containing a carbon bonded to the oxygen.

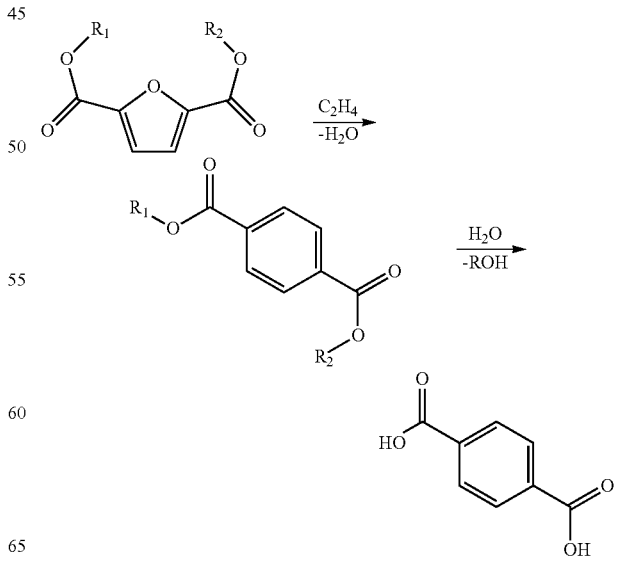

Other derivatives of DMF will produce different reaction products, which can undergo different reactions to produce the terephthalic acid (when terephthalic acid is the desired end product). The following discussion is a non-exclusive list of some of the types of derivatives of DMF that can be used. For example, if an aldehyde derivative of DMF is used, a corresponding benzaldehyde derivative is obtained by reaction with ethylene. The benzaldehyde derivative can be subsequently oxidized by contacting with an oxidizing agent to obtain terephthalic acid. Alternatively, the benzaldehyde derivative can be subsequently selectively hydrogenated, for instance over a noble metal catalyst, to obtain the corresponding benzyl alcohol derivative and/or methyl aromatic. The benzyl alcohol derivative and/or methyl aromatic can then be contacted with an oxidizing agent to obtain terephthalic acid.

The reaction scheme below illustrates one example of the reaction of an aldehyde derivative of DMF to form terephthalic acid either in two steps or three steps.

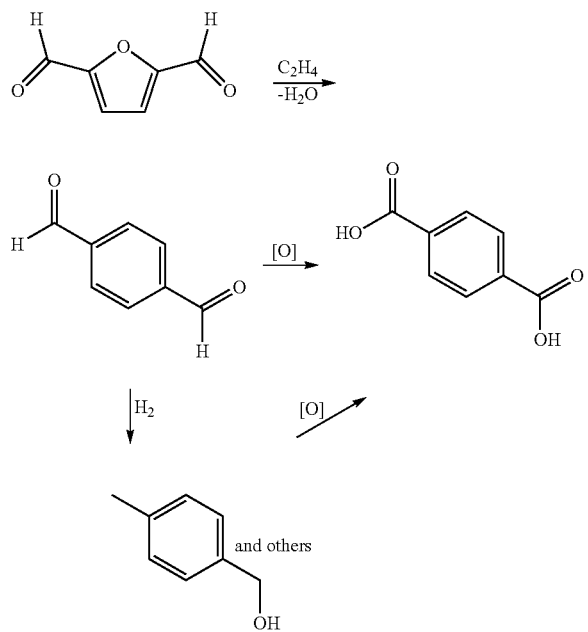

If an ether derivative of DMF is used, the corresponding benzyl ether derivative is obtained by reaction with ethylene. The benzyl ether derivative can be subsequently hydrolyzed by contacting with an acid or base to form the corresponding benzyl alcohol derivative. The benzyl alcohol derivative can then be oxidized with or without isolation to form terephthalic acid. Alternatively, the benzyl ether derivative can be oxidized directly to terephthalic acid.

The reaction scheme below illustrates one example of the reaction of an ether derivative of DMF to form terephthalic acid in two or three steps.

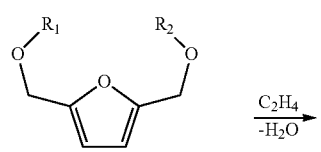

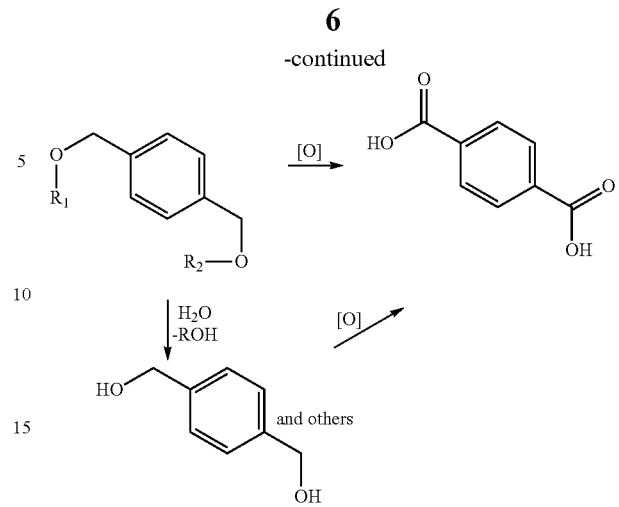

If a halide derivative of DMF is used, the corresponding halomethylaromatic is obtained by reaction with ethylene. The halomethylaromatic can be subsequently reacted with a hydroxyl containing base to form the corresponding benzyl alcohol derivative and subsequently oxidized to obtain terephthalic acid. Alternatively, the halomethylaromatic can be oxidized directly by contacting with an oxidizing agent.

The reaction scheme below illustrates one example of the reaction of a halide derivative to form terephthalic acid in two or three steps, where X is F, Cl, Br or I.

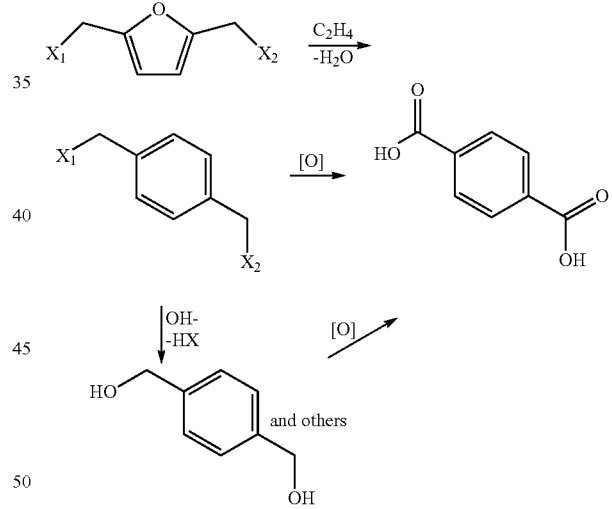

If an acid halide derivative of DMF is used, the corresponding terephthalate acid halide and/or ethyl terephthalate ester is obtained by reaction with ethylene. The corresponding terephthalate acid halide and/or terephthalate ester can be subsequently hydrolyzed by contacting with aqueous acid or base to obtain terephthalic acid.

If an amide derivative of DMF is used, the corresponding terephthalamide and/or ethyl terephthalate ester is obtained by reaction with ethylene. The corresponding terephthalamide and/or terephthalate ester can be subsequently hydrolyzed by contacting with aqueous acid or base to obtain terephthalic acid.

If an anhydride derivative of DMF is used, the corresponding terephthalate anhydride, and/or terephthalic acid, and/or ethyl terephthalate ester is obtained by reaction with ethylene.

The corresponding terephthalate anhydride and/or ethyl terephthalate ester can be subsequently hydrolyzed by contacting with aqueous acid or base to obtain terephthalic acid.

The reaction scheme below is a general depiction of one example of the reaction of an acid halide derivative of DMF, an amide derivative of DMF, or an anhydride derivative of DMF, where $A_1$ and/or $A_2$ are a halide (F, Cl, Br or I) for an acid halide, —$NH_2$ for an amide or —OCOOR for an anhydride where R is H or a hydrocarbon.

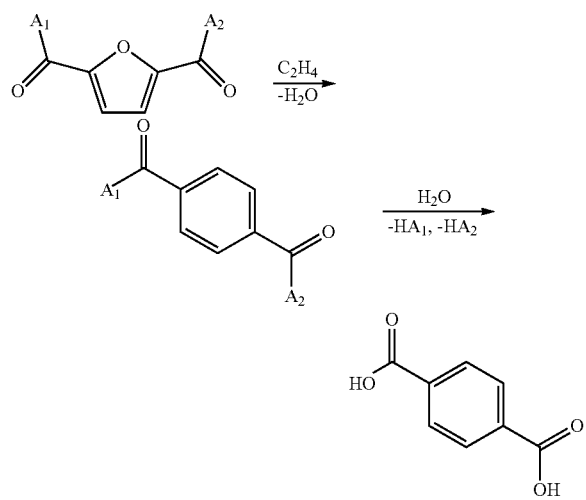

If an alcohol derivative of DMF is used, the corresponding benzyl alcohol is obtained by reaction with ethylene. The benzyl alcohol derivative can be oxidized to obtain terephthalic acid by contacting with an oxidizing agent.

The reaction scheme below is an illustration of one example of the reaction of a DMF derivative to form terephthalic acid in two steps.

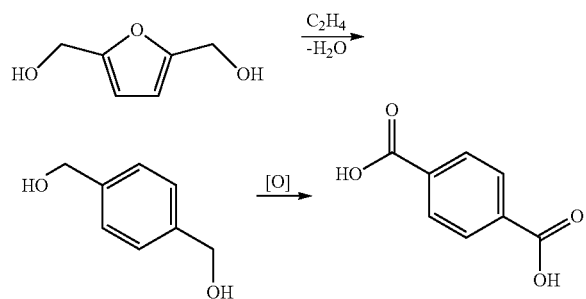

The reaction takes place in a solvent. In some embodiments, the solvent can be nonpolar, while in other embodiments, polar aprotic solvents can be used. While not wanting to be bound by theory, the use of a protic solvent is thought to result in catalyst deactivation due to poisoning of Brönsted acid sites. In some embodiments, a portion of the para-xylene derivative product is used as the solvent. Suitable solvents include, but are not limited to, alkanes, halogenated alkanes (such as dichloromethane), cycloalkanes, aromatics, alkylaromatics (such as toluene), sulfoxides (such as dimethylsulfoxide), ethers (such as diethyl ether, tetrahydrofuran, or dioxane), alkyl amides (such as dimethylformamide or N-methylpyrrolidone), ionic liquids, ketones, nitriles, esters, or combinations thereof. Alkanes and cycloalkanes are preferred solvents.

Elimination of sources of water, and/or removal of the water generated in the reaction may result in more complete conversion. While not wanting to be bound by theory, removal of water is thought to increase the thermodynamic favorability of the dehydration step of the reaction. Thus, the preferable choices for solvent are solvents such as alkanes which do not generate water by solvolysis. Additionally, the conversion may be increased by removal or capture of water in-situ such as for example, by a water-miscible ionic liquid that is immiscible in the hydrocarbon phase, by addition of a drying agent such as a molecular sieve (e.g. 13X or 3A), by a hydroscopic salt such as magnesium sulfate, or by an anhydride such as acetic anhydride.

Examples of suitable catalysts are those having Brönsted acidity. In some embodiments, the catalyst also has Lewis acidity. The catalyst can also include electron-rich metal promoters. The Brönsted function is thought to catalyze dehydration, while the Lewis acid function and the metal promoter catalyze the cycloaddition. These catalyst functions are preferably found in close proximity, such as in the same 2.4 nm unit cell in the case of Ag-exchanged Y-zeolite, or at the interfaces of tungsten oxide particles and zirconia support in tungstated zriconia.

Suitable catalysts include, but are not limited to, solid acid catalysts, metal oxides, ionic liquids, and zeolites. In some embodiments, the solid acid catalyst comprises oxides of a metal or oxides of mixed metals on zirconia or sulfated zirconia. Suitable oxides of metals include, but are not limited to oxides of tungsten, oxides of molybdenum, oxides of lanthanum, oxides of cerium, oxides of yitrium, oxides of titanium, oxides of scandium, oxides of vanadium, oxides of chromium, oxides of hafnium, oxides of niobium, oxides of tantalum and combinations thereof.

Brönsted acid catalysts improve the rate of dehydration of the cycloadduct and may include zeolites, amorphous silica-alumina, solid phosphoric acid, silica-aluminum phosphates, tungstated zirconia, sulfated zirconia, titanium silicalite, and metal oxides such as niobia. Brönsted acid catalysts may also be homogeneous catalysts including strong acids such as nitric, sulfuric, hydrochloric, hydrobromic, hydroiodic and perchloric acid, and weak acids such as carboxylic acids. Homogenous Brönsted acids can also be ionic liquids where either the cation or anion is Brönsted acidic. For instance, Brönsted acidic cations can include pyridinium, 1-alkylpyraziniums, 1-alkylpyrimidiniums, pyrrolinium, mono-N-alkyl pyrrolodiniums, mono-N-alkylpiperidiniums, 1-alkylimidazoliums, 1-alkyl pyrazoliums, and di- or tri-alkyl ammoniums. Brönsted acidic anions include bisulfate and hydrogenphosphate, dihydrogenphosphate, alkylphosphate and dialkylphosphates The catalyst may have Lewis acidity. Lewis acidity is thought to increase the rate of cycloaddition. Lewis acids are used to withdraw electron density from the reactants (from the dienophile in traditional Diels-Alder cycloaddition reactions or from the diene in inverse electron-demand Diels-Alder cycloaddition reactions). In the examples, H—Y zeolite and tungstated zirconia are used as a Lewis acid. Other Lewis acids may include other zeolites, metal-exchanged zeolites (e.g. Na—Y), gamma-alumina, amorphous silica-alumina, aluminum phosphates, aluminum silicon phosphates, zirconia, titanium oxides, zinc oxide, other Lewis acidic metal oxides, aluminum halides and other Lewis acidic metal halides (such as iron chloride and zinc chloride), supported aluminum halides and other Lewis acidic supported metal halides. The Lewis acid can also be homogenous, such as a melt or solution of aluminum chloride, lithium chloride, iron chloride, zinc chloride, zinc iodide, boron trifluoride and solutions of salts of scandium, titanium, yttrium, zirconium, lanthanide series metals, hafnium, tin, antimony and other Lewis acidic metals. The homogenous Lewis acid can also be an ionic liquid such as ionic liquids containing haloaluminate, halostannate, or halozincate anions.

A preferred catalyst is tungstated zirconia. While not wanting to be bound by theory, one possible explanation for the higher selectivity obtained using tungstated zirconia relative to zeolites may be that the zeolite catalysts are much better catalysts for ethylene activation than tungstated zirconia. As is shown in the examples, this is consistent with the high coke yields observed when using zeolite catalysts as well as the higher proportion of ethyl-ester substituents compared to methyl substituents which are observed using zeolite catalyst. A probable explanation for the formation of ethyl esters is by acid-catalyzed trans-esterification with ethylene. The orange and brown color that was observed in the zeolite catalyzed reaction products may also indicate a propensity for Y-zeolite to catalyze oligomerization. The lower amount of coke, lower amount of transesterification of methyl esters to ethyl esters and the lack of orange color, all indicate that tungstated zirconia is not a strong activator of ethylene and may explain its high selectivity compared to zeolites and make it a preferred catalyst for this reaction.

The metal promoter increases the reaction rate of the cycloaddition. The metal should have a low work function, such that electron donation from metal to diene or dienophile is favorable. Any metal or alloy with a work-function less than that of Pt may work as a catalyst, so long as it is not so electron rich that it would oxidize to an inactive state under reaction conditions. Among others, suitable metals may include Ag, Au, Bi, Cd, Co, Cr, Cu, Fe, Hg, In, Mo, Nb, Ni, Pd, Re, Rh, Ru, Ta, Ti, V, or W. The oxidation state may be adjusted via oxidation or stabilized by incorporation into the solid support to further adjust the reaction conditions to accommodate either the furan or the olefin derivative. For instance, lower metal oxidation states can be important for facilitating the inverse Diels-Alder reaction in which the diene rather than the dienophile carries electron withdrawing groups.

The dienophile contains an unsaturated 2-carbon unit. Generally, ethylene is used as a dienophile. Alternatively, acetylene may be used as a dienophile. If acetylene is utilized as dienophile, the cycloadduct contains two rather than one C=C double bond, and spontaneous dehydration to form an aromatic ring cannot occur. Instead, the cycloadduct can be isolated, and one double bond selectively hydrogenated using hydrogen over a hydrogenation catalyst to form the desired cycloadduct which can subsequently be dehydrated over a Brönsted acid or base catalyst to form the para xylene derivative. Alternatively, hydrogen can be added in-situ to accomplish the hydrogenation of the second double bond, and acetylene kept in sufficient excess to avoid its full hydrogenation. Derivatives of ethylene and acetylene can also be used, such as vinyl chloride and vinyl ethers. If vinyl chloride or vinyl ether is used as the dienophile, the product is a para xylene derivative with a chloride or hydroxyl derivative at a third position. This substituent can be removed using known chemistries such as catalytic hydrogenation, reaction with metal hydride or reaction with other reducing agents known in the art. Use of vinyl chloride or vinyl ether would accelerate the cycloaddition rate due to an electron withdrawing substituent on the dienophile.

The process produces a para-xylene derivative. The para-xylene derivative contains at least one atom bonded to at least one of the methyl carbons that is not hydrogen or carbon. In some embodiments, the para-xylene derivative itself is recovered. For example, dimethyl terephthalate can be used as a polyester monomer, and so it might be a desired product.

The FIGURE illustrates one embodiment of an integrated process 100 for the esterification of FDCA to DM-FDCA and hydrolysis of DM-FDCA to terephthalic acid. A feed 105 comprising a derivative of DMF, such as FDCA, is mixed with an alcohol 110, such as methanol, in a mixing zone 115. The mixture 120 is heated in a heater 125, and the heated mixture 130 is introduced into a reaction zone 135. Alternatively, the mixture could be heated using another method, including, but not limited to, heat exchangers, or steam. The heating can take place in a separate zone or in the reaction zone itself. The methanol reacts with the FDCA in the presence of a dilute acid catalyst to form DM-FDCA. Preferred reaction conditions include about 180° C. to about 220° C. at pressure sufficient to keep the alcohol a liquid (about 240 kPa for methanol). The acid catalyst can be homogeneous or heterogeneous. If a homogeneous catalyst is used, a continuous stirred tank reactor (CSTR) can be used. If a heterogeneous catalyst is used, a fixed bed reactor could be used. Desirably, water is continuously removed from the reaction zone 135 to improve conversion.

The reaction mixture 140 is sent to a crystallizer 145 where it is crystallized followed by a solid/liquid separation. For example, water 150 can be added to the reaction mixture to crystallize DM-FDCA. The liquid stream 180 contains dilute methanol and water.

The DM-FDCA 155 is sent to the Diels-Alder reaction zone 160. The Diels-Alder reaction zone 160 contains the catalyst having Brönsted acidity and optionally Lewis acidity and an optional metal promoter, as well as solvent. Suitable reaction conditions include temperature of about 25 to about 300° C. and total reaction pressure of about 101 kPa to about 12.2 MPa (1-120 atmosphere). Preferred conditions include a temperature of about 100 to about 250° C. and pressure of about 3.0 MPa to about 12.2 MPa (30-120 atmospheres). A dienophile 165, such as ethylene, is added to the Diels-Alder reaction zone 160. The DM-FDCA reacts with the ethylene and forms dimethyl terephthalate.

The dimethyl terephthalate 170 is sent to a reaction zone 175, along with water. The stream 180 from the separator 145 is sent to the reaction zone 175 where the dimethyl terephthalate is hydrolyzed to terephthalic acid and methanol. Suitable reaction conditions include temperature of about 25 to about 250° C. and total reaction pressure of about 101 kPa to about 10.1 MPa (1-100 atmosphere). Preferred conditions include temperature of about 50 to about 200° C. and pressure of about 101 kPa to about 2.0 MPa (1-20 atmospheres). The amount of water added must be sufficient to hydrolyze the dimethyl terephthalate—or at least two molar equivalents of water to dimethyl terephthalate. Excess water may be added to accelerate the hydrolysis reaction. Also, a suitable hydrolysis catalyst, such as sulfuric acid, or a solid acid such as sulfonated polystyrene resin may also be present in the hydrolysis reaction zone 175.

The effluent 185 is sent to a separator 190 where the solid terephthalic acid product 195 is separated from the water 200.

A stream of methanol 205 can be removed from the reaction zone 175 and recycled to the mixing zone 115.

The heat from the Diels-Alder reaction zone 160 can be used to heat the reaction zone 175, if desired.

EXAMPLES

In the examples that follow, a 300 cc Hastelloy-C autoclave fitted with a gas-entrainment stirrer was loaded with 0.5-1.0 g feed, 123 mL solvent and 1-2 g catalyst. At room temperature, the reactor was purged with nitrogen, pressurized with approximately 345 kPa (g) (3 atm) nitrogen and then pressurized with ethylene while stirring at 1500 rpm. The pressure was monitored until a constant pressure was reached (pressure decreases were observed due to dissolution of ethylene) and then pressurized to 2.8 MPa (g) (28 atm) total pressure. The reactor was sealed and heated to 225° C., and held at that temperature for approximately 5 hours. Pressure at reaction temperature was 8.3-11.0 MPa (g) (82-109 atm). The heat was removed and the reactor was allowed to cool overnight while stirring. Analysis was conducted by adding chloroform to the product slurry to dissolve all furanate and terephthalate components. Products were identified by gas chromatography-mass spectrometry (GC-MS) and comparison to known standards where available, and quantified by GC with a flame ionization detector (FID).

Reactions of FDCA

Comparative Example 1

In this example, 1 g FDCA was the feed, no catalyst was used, and the solvent was butanol. The reaction pressure was 10.0 MPa (g) (99 atm), the temperature was 225° C., and the reaction time after reaching temperature was 5 hours. Under these conditions, FDCA is expected to undergo esterification reaction to form dibutyl-FDCA. GC-MS showed conversion of FDCA to the di-butyl ester derivative of FDCA and the butyl-ester derivative of FDCA, as well as a trace amount of dibutyl-terephthalate.

Example 1

In this example, 1 g FDCA was the feed, the solvent was butanol, and 2 g of catalyst was used. Two different catalysts were used in separate reactions: 1) either Norit® CA1 activated carbon (available from Sigma-Aldrich) which had been washed 3 times with 10 wt % nitric acid or 2) steamed HY zeolite with Si/Al elemental mole ratio of 2.57 ($SiO_2/Al_2O_3$ ratio of 5.14). The reaction pressure during the reaction using activated carbon catalyst was 9.2 MPa (g) (91 atm), and it was 8.6 MPa (g) (85 atm) using the HY zeolite. The reaction temperature was 225° C., and the reaction time after reaching temperature was 5 hours. Under these conditions, FDCA is expected to undergo esterification reaction to form dibutyl-FDCA. GC-MS showed conversion of FDCA to the di-butyl ester derivative of FDCA and the butyl-ester derivative of FDCA using either catalyst, as well as a trace amount of dibutyl-terephthalate in the reaction using the HY zeolite. The products in these reactions also contained 0.3-0.8 wt % water, which is due to the production of two moles of water from the esterification of FDCA plus one mole from the dehydration of the cycloadduct plus water resulting from solvolysis of butanol. The high amount of water present may be responsible for the low yield, due to inhibition of the dehydration of the cycloadduct.

Reactions of DM-FDCA

To eliminate water and protic solvent from the reaction, all subsequent tests were completed using n-heptane as the solvent. The solvent was not dried, but water analysis showed that only 18 ppm was present, which is considerably less than the amount of water that is theoretically generated in the dehydration of the bicyclic adduct. All catalysts used were dried at 150-175° C., followed by calcination at 500° C. for metal-free zeolites, or 650° C. for tungstated zirconia. DM-FDCA (obtained commercially) was used as the feed. 0.59 g was used in each run (in 84 g heptane). GC-MS was used to identify products which were subsequently quantified by GC with FID detector. In a blank run (with ethylene but no catalyst—comparative example 2), no products other than DM-FDCA were observed. In runs with catalyst, DM-FDCA appears to undergo trans-esterification with ethylene. This results in ethyl-methyl diesters of FDCA and diethyl esters of FDCA. The desired products, the corresponding ethyl and methyl terephthalate esters, are also observed. Trace amounts of benzoate and methyl-furan esters were also observed by GCMS, but in insufficient amounts to quantify by GC with FID. Generally, ethyl groups account for about 50% of the substituents in the tungstated zirconia catalyzed reactions and 60-75% of the substituents in the zeolite catalyzed reactions.

The results from the several reactions completed are shown in Table 1. Furan conversion is one minus the total moles of furan esters (dimethyl+ethyl,methyl+diethyl) detected at the end of reaction divided by the moles of DM-FDCA feed at the beginning of the reaction. Terephthalate yield is the total moles of terephthalate esters divided by moles of feed. Terephthalate selectivity is total moles of terephthalate esters as a percent of moles of converted furans. Mass balance is total moles of detected furan esters and terephthalate esters divided by moles of DM-FDCA in the feed. % Ethyl substituent is the proportion of ethyl ester substituents in the furan esters and terephthalate esters (i.e., 2 substituents per molecule). Coke yield is moles of carbon remaining on the catalyst after Soxhlet extraction in chloroform, divided by moles of carbon in the DM-FDCA feed. Numbers in parentheses are based on mass loss in TGA at greater than 400° C. rather than Soxhlet extraction. Note that ethylene may also be a source of coke but is not considered in the coke yield basis.

Comparative Example 2

In this example, 0.7 g DM-FDCA (obtained commercially) was the feed, no catalyst was used, and the solvent was n-heptane. Reaction pressure was 9.9-10.3 MPa (g) (98-102 atm), reaction temperature was 225-227° C., and reaction time was 5.5 hours. The final product was a clear liquid with very slight yellow color, and a white solid. GC-MS showed no products present other than the reactant itself.

Example 2

In this example 0.57 g DM-FDCA was the feed. Steamed HY zeolite with Si/Al elemental mole ratio of 2.57 was used as the catalyst and was dried at 150° C. for 3 hours and calcined at 500° C. for 6 hours prior to reaction. The pre-calcination weight was 2 grams (for comparison to example 1), but the post-calcination weight was 1.58 g. n-Heptane was loaded as the solvent. The reaction pressure was 9.1-9.2 MPa (g) (90-91 atm), and the temperature was 225-226° C. The reaction was held at temperature for 5.5 hours. The result was an orange-brown solid (spent catalyst and coke) and a clear liquid. Products, analyzed by GC, are shown in Table 1 (as mol % of initial moles DM-FDCA added). Furans conversion was 83.0%. The total yield of terephthalates was 3.4%, and terephthalate selectivity was 4.1%. The mass balance of furans+terephthalates was 20.4%. In the total furan and terephthalate products 63% of the esters were ethyl esters (the remaining portion were methyl esters). Coke yield was 59%. Compared to run 1, utilizing an ester feed and non-protic solvent has a significant effect.

Example 3

In this example 0.59 g DM-FDCA (obtained commercially) was the feed. The material used here as catalyst used here is described in example 7 of U.S. Pat. No. 6,380,428, with an additional drying and reduction treatment. It was silver-exchanged LZ-210 Y-zeolite (described in U.S. Pat. No. 4,503,023) oil-dropped spheres that contained 20% silica binder and 80% zeolite, where the zeolite component had $SiO_2/Al_2O_3$ mol ratio of 10. That material was dried at 300° C. for 2 hours and reduced at 250° C. in hydrogen for 2 hours prior to reaction. The catalyst was 9.34% silver (by weight, dry basis). n-Heptane was loaded as the solvent, along with 1.59 g of dried reduced catalyst. The reaction pressure was 9.9-10.1 MPa (g) (98-100 atm), and the temperature was 224-226° C. The reaction was held at temperature for 5.5 hours. The result was an orange-brown solid (spent catalyst and coke) and a clear liquid. Products, analyzed by GC, are shown in Table 1 (as mol % of initial moles DM-FDCA added). Furan conversion was 85.6%. The total yield of terephthalates was 8.5%. Selectivity to terephthalates was 9.9%. The mass balance of furans+terephthalates was 22.9%. Significant peaks were observed in GC corresponding to poly-alkylated benzenes, indicating that coke and coke-precursors accounts for more than the remaining mass balance of furanic feed. In the total furan and terephthalate products, 71% of the esters were ethyl esters (the remaining portion were methyl esters).

Example 4

LZ-210 Y-zeolite (described in U.S. Pat. No. 4,503,023) oil-dropped spheres that contained 20% silica binder and 80% zeolite, where the zeolite component had $SiO_2/Al_2O_3$ mol ratio of 9, was used as catalyst. 83.71 g heptane was loaded as the solvent, along with 1.62 g of calcined catalyst and 0.60 g of DM-FDCA. The reaction pressure was 10.0-10.3 MPa (g) (99-102 atm), and the temperature was 225-227° C. The reaction was held at temperature for 5.5 hours. The result was an orange-brown solid (spent catalyst and coke) and a clear liquid. Products, analyzed by GC, are shown in Table 1 (as mol % of initial moles DM-FDCA added). Furan conversion was 77.3%. The total yield of terephthalates was 7.4%. Selectivity to terephthalates was 9.6%. The mass balance of furans+terephthalates was 30.2%. In the total furan and terephthalate products, 77% of the esters were ethyl esters (the remaining portion were methyl esters).

Example 5

LZ-210 was also tested at a higher temperature, 275° C., to try to improve activity both by thermal activation and by preventing water adsorption to the zeolite. This was unsuccessful. The slurry was black. Products that were observed in lower temperature reactions were not seen in the GC from the higher temperature reaction, and a continuum of unidentified products were generated.

Example 6

Tungstated zirconia was also tested as a catalyst (replicate examples 6A and 6B). The catalyst contained 12.5 wt % tungsten on volatile free basis. Prior to the reaction, the catalyst was calcined at 650° C. for 4 hours after drying at 175° C. for 3 hours. 1.6 g of catalyst was used with 84 g of heptane as the solvent and 0.58 g of DM-FDCA. In one of the replicate 225° C. reactions, the furan conversion was 69%, and in the other it was 96%. Both replicate runs had much higher terephthalate yield (22.1 and 15.3%) than the Y-zeolite runs, and higher terephthalate selectivity (32.1 and 15.9%). The mass balance of furan and terephthalate products on the furan feed basis was 53.1% and 19.2% in the two runs. 58% of the ester substituents were ethyl as opposed to methyl in the furan and terephthalate products in both runs. The coke yield was 26% in one of the runs and not analyzed in the other.

Example 7

Example 7 was completed using the same catalyst as in example 6, but at lower temperature 211° C. to determine if selectivity would improve. While the coke yield was only 15-18% (less than it was at 225° C.), the terephthalate selectivity was 20.5%, similar to the higher temperature examples.

The products from all runs with tungstated zirconia were slightly grey, but not orange or brown like the reaction products obtained using Y-zeolite, Ag/LZ-210, or LZ-210.

The coke yield was also considerably lower than the zeolite runs, as was the amount of ethyl ester substituents. These results indicate that ethylene may not be activated as extensively on the catalyst and/or the reactions that lead to coke are not promoted. Additionally, the catalyst is not active for cracking of the solvent or product.

TABLE 2

Furan conversion, terephthalate yield and selectivity, mass balance, % ethyl substituents, and coke yield (coke yield in parentheses was measured by TGA, others measured by soxhlet extraction and combustion analysis)

| Example | Catalyst | Si/Al$_2$ | Temp ° C. | Furan Conv. | Terephthalate yield | Terephthalate selectivity | Mass balance | % Ethyl substituents | Coke yield FDCA basis |
|---|---|---|---|---|---|---|---|---|---|
| 2 | Y-zeolite (calc 500° C.) | 5 | 225 | 83.0% | 3.4% | 4.1% | 20.4% | 63% | (59%) |
| 3 | Ag/LZ-210 (reduced 250 ° C.) | 10 | 225 | 85.6% | 8.5% | 9.9% | 22.9% | 71% | 104% (94%) |
| 4 | LZ-210 (calc 500° C.) | 9 | 225 | 77.3% | 7.4% | 9.6% | 30.2% | 77% | Not analyzed |
| 5 | LZ-210 (calc 500° C.) | 9 | 275 | | | Black residue | | | |
| 6A | WOx/ZrOx (calc 650° C.) | | 225 | 69.1% | 22.1% | 32.1% | 53.1% | 58% | (26%) |
| 6B | WOx/ZrOx (calc 650° C.) repeat | | 225 | 96.1% | 15.3% | 15.9% | 19.2% | 58% | Not analyzed |
| 7 | 211° C. WOx/ZrOx (calc 650° C.) | | 211 | 77.5% | 15.9% | 20.5% | 38.4% | 52% | 15% (18%) |

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process of making terephthalic acid or a derivative of terephthalic acid comprising:
    reacting a diester derivative of 2,5-dimethylfuran, with a dienophile containing an unsaturated 2-carbon unit, in the presence of a catalyst comprising a metal oxide having Brönsted acidity to form a para-xylene derivative and wherein the catalyst further comprises a metal promoter; and
    optionally reacting the para-xylene derivative to terephthalic acid.

2. The process of claim 1 wherein the catalyst further has Lewis acidity.

3. The process of claim 1 wherein the catalyst comprises a Bronsted acid tungstated zirconia.

4. The process of claim 1 wherein the catalyst is selected from solid acid catalysts, metal oxides, ionic liquids, and zeolites.

5. The process of claim 4 wherein the solid acid catalyst comprises oxides of a metal on zirconia or sulfated zirconia.

6. The process of claim 1 wherein the dienophile is ethylene, acetylene, vinyl chloride, or a vinyl ether.

7. The process of claim 1 wherein the reaction takes place in a solvent.

8. The process of claim 7 wherein the solvent comprises alkanes, halogenated alkanes, cycloalkanes, aromatics, alkylaromatics, sulfoxides, ethers, alkyl amides, ionic liquids, ketones, nitriles, or combinations thereof.

9. The process of claim 7 wherein the solvent comprises the p-xylene derivative.

10. The process of claim 1 wherein the reaction takes place at a temperature in a range of about 80° C. to about 300° C., and at a pressure of at least about 690 kPa.

11. The process of claim 1 further comprising:
    reacting 2,5-furandicarboxylic acid and an alcohol to form the ester of the 2,5-furandicarboxylic acid; and
    wherein reacting the derivative of 2,5-dimethylfuran with the dienophile comprises reacting the ester of the 2,5-furandicarboxylic acid with the dienophile.

12. The process of claim 1 wherein the ester derivative of 2,5-dimethylfuran is obtained from saccharide-containing biomass.

13. The process in claim 1 wherein the reaction of the para-xylene derivative to form the terephthalic acid comprises at least one of a hydrolysis reaction, an oxidation reaction, or a nucleophilic substitution reaction.

14. The process in claim 1 in which water is removed, adsorbed or reacted during the reaction of the ester derivative of 2,5-dimethylfuran with the dienophile.

15. A process of making terephthalic acid comprising:
    reacting 2,5-furandicarboxylic acid and an alcohol to form an ester of the 2,5-furandicarboxylic acid, wherein the 2,5-furandicarboxylic acid is obtained from saccharide-containing biomass;
    removing water while reacting the 2,5-furandicarboxylic acid and the alcohol;
    reacting the ester of the 2,5-furandicarboxylic acid with a dienophile containing an unsaturated 2-carbon unit in the presence of a solid acid catalyst comprising a metal oxide having Brönsted acidity and a solvent at a temperature in a range of about 80° C. to about 300° C., and at a pressure of at least about 690 kPa to form a derivative of terephthalic acid; and
    hydrolyzing the derivative of terephthalic acid to terephthalic acid.

16. The process of claim 15 wherein the solid acid catalyst comprises a Bronsted acid tungstated zirconia.

17. The process of claim 15 wherein the dienophile is ethylene, acetylene, vinyl chloride, or a vinyl ether.

18. The process of claim 15 wherein the catalyst further has Lewis acidity.

19. The process of claim 15 wherein the solvent comprises alkanes, halogenated alkanes, cycloalkanes, aromatics, alkylaromatics, sulfoxides, ethers, alkyl amides, ionic liquids, ketones, nitriles, or combinations thereof.

* * * * *